United States Patent
Mah

(10) Patent No.: US 10,441,395 B2
(45) Date of Patent: Oct. 15, 2019

(54) DEVICES AND METHODS FOR SHIPPING AND ANALYZING DENTAL IMPRESSIONS

(71) Applicant: James Mah, Las Vegas, NV (US)

(72) Inventor: James Mah, Las Vegas, NV (US)

(*) Notice: Subject to any disclaimer, the term of this patent is extended or adjusted under 35 U.S.C. 154(b) by 1119 days.

(21) Appl. No.: 14/806,458

(22) Filed: Jul. 22, 2015

(65) Prior Publication Data

US 2017/0020642 A1    Jan. 26, 2017

(51) Int. Cl.
| | | |
|---|---|---|
| *A61C 19/02* | (2006.01) | |
| *A61C 19/05* | (2006.01) | |
| *G01N 24/08* | (2006.01) | |
| *G01N 23/046* | (2018.01) | |

(52) U.S. Cl.
CPC .............. *A61C 19/02* (2013.01); *A61C 19/05* (2013.01); *G01N 23/046* (2013.01); *G01N 24/08* (2013.01)

(58) Field of Classification Search
CPC ......... A61C 19/02; A61C 19/05; A61C 11/00; G01N 23/046; G01N 24/08
USPC ................................. 206/63.5, 368; 433/77
See application file for complete search history.

(56) References Cited

U.S. PATENT DOCUMENTS

| | | | | | |
|---|---|---|---|---|---|
| 3,552,257 | A | * | 1/1971 | Tanabe | F16B 35/02 411/368 |
| 3,936,937 | A | * | 2/1976 | Gordon | A61C 11/00 433/77 |
| 4,763,791 | A | * | 8/1988 | Halverson | A61C 9/00 206/369 |
| 7,188,729 | B2 | * | 3/2007 | DeJonge | B65D 83/0463 206/1.5 |
| 7,201,271 | B1 | * | 4/2007 | Saad | A45C 11/00 132/315 |
| 8,162,140 | B2 | * | 4/2012 | Hansen | A61B 10/0096 206/438 |
| 8,220,636 | B2 | * | 7/2012 | Beecroft | B65D 83/0472 206/1.5 |
| 2004/0244805 | A1 | * | 12/2004 | Cook | B65D 43/164 128/859 |
| 2008/0283422 | A1 | * | 11/2008 | Jansheski | B65D 43/164 206/63.5 |
| 2010/0181214 | A1 | * | 7/2010 | Brown | A61C 19/02 206/63.5 |
| 2011/0183293 | A1 | * | 7/2011 | Tchouangang | A61C 13/0024 433/213 |

(Continued)

FOREIGN PATENT DOCUMENTS

DE           9116942        * 11/1991    ............ A61C 9/0006

*Primary Examiner* — Chun Hoi Cheung

(57) ABSTRACT

A shipping container that is configured to store, protect, and transport a dental impression is disclosed. The shipping container includes an exterior surface that encloses an interior area; a support located within the interior area that is configured to receive an impression tray that includes a patient's dental impression; and a means attached to or integrally formed with the support that is configured to hold the impression tray in place on the support and to position the impression tray in a standardized orientation. The shipping container, including its exterior surface and internal support(s), are made of a material that will not interfere with a selected non-invasive imaging scan. The shipping container is configured and used to obtain a digital scan of the dental impression, without the need to open the shipping container or directly handle the dental impression.

18 Claims, 3 Drawing Sheets

(56) References Cited

U.S. PATENT DOCUMENTS

2013/0180870 A1\* 7/2013 Nihei ..................... A61B 50/00
206/63.5

\* cited by examiner

DEVICES AND METHODS FOR SHIPPING AND ANALYZING DENTAL IMPRESSIONS

FIELD OF THE INVENTION

The field of the present invention relates to devices and methods for shipping and analyzing dental impressions.

BACKGROUND OF THE INVENTION

Dentists, clinics, and other dental-related facilities often ship dental impressions of patients to a laboratory, where the impressions are used in subsequent fabrication/laboratory procedures. In many cases, the dental impressions consist of materials such as polyvinylsiloxane (PVS) or alginate, with such materials being supported in a container (such as an impression tray). Such laboratories use the impressions to produce and provide dentists with certain restorations (e.g., crowns and bridges), guides for surgery, splints, dentures, bleaching trays, orthodontic appliances, and other products for the corresponding patients.

The impressions are frequently transferred to such laboratories by first wrapping the impressions with bubble wrap, paper towels, foam, Styrofoam sheets, or small plastic bags, which are then placed into a shipping container. The shipping container is typically comprised of paper, cardboard or plastic. The shipping container is often shipped alone, or may be packaged together with other items, for transit by courier, delivery services, expedited shipping companies, or the postal service.

Once the shipping container is received at the dental laboratory, the impression contained therein undergoes several processing steps. First, the shipping container is opened and the impression is visually inspected. Next, the impression is disinfected with bactericidal, antiviral, and antifungal agents, which reduce or eliminate certain biohazards that may exist on the surface of the impression. The impression is also labelled for tracking purposes and finally poured up in stone/gypsum (or imaged using a laser or x-ray system) to produce a physical or digital model of the impression.

There are many problems with the current process outlined above. The impression is often distorted and damaged during the packaging and shipping step, with the choice of wrapping material to cushion the impression providing various degrees of protection. In addition, the shipping container is often too small, which leads to compression of the impression and resultant distortion. In addition, insufficient amounts of protective packaging material often lead to excess space around the impression and damage during shipping. The position of the impression inside the container may also influence the quality of the impression once it is received by the laboratory. For example, if the impression of a patient's lower jaw is inverted and allowed to rest on its heels (the posterior extension of the impression material), the area can be easily distorted and damaged.

Still further, once the shipping container arrives at the laboratory, the impression must be treated as a biohazard. This requires that the laboratory technicians be trained to handle such biohazards (and the receiving area within the laboratory must include a quarantined area where various precautions are exercised, such as the use of protective gloves, eyewear, and gowns). In addition, as mentioned above, the impression itself must be disinfected and decontaminated using harsh chemicals to reduce and eliminate bacteria, viruses, and fungi (and such chemicals have been found to cause minor amounts of distortion of the impression as well). These processes and precautions require substantial technician labor—and expose technicians to certain risks associated with using harsh disinfecting chemicals.

As the following will demonstrate, the device and methods of the present invention address many of these problems with the current processes (and shipping containers) described above.

SUMMARY OF THE INVENTION

According to certain aspects of the invention, a shipping container that is configured to store, protect, and transport a dental impression is provided. The shipping container includes an exterior surface that encloses an interior area. The interior area of the shipping container includes a support (or, in some embodiments, multiple supports) that is configured to receive an impression tray that includes and holds a patient's dental impression. In addition, the shipping container includes a means for holding the impression tray in place on the support and to position the impression tray in a standardized orientation. The invention provides that the exterior surface and support(s) are comprised of a material that will not interfere with a selected non-invasive imaging scan, such that the dental impression (and, optionally, a patient's bite registration disposed in the shipping container as well) may be imaged without the need to open the shipping container (or directly handle the dental impression).

In certain embodiments, the invention encompasses the shipping container itself, along with an impression tray that is configured as described herein. More particularly, in certain embodiments, the means attached to or integrally formed with the support may consist of a rod that extends perpendicular from a top surface of the support. In that case, the impression tray may include a handle and an aperture located in the handle that is configured to receive the rod (i.e., the rod may be disposed through the aperture), such that the impression tray is held in place on the support and is positioned in a standardized orientation. As described further below, the invention provides that other mechanical means for immobilizing the impression tray on the support may also be employed. The invention provides that the exterior surface and support of the shipping container are preferably comprised of a material selected from the group consisting of acrylic materials, plastic materials, paper, cardboard, foam, and wood materials, when the non-invasive imaging scan is a radiographic imaging scan. Importantly, as described further below, the invention provides that the material used to form the exterior surface and support of the shipping container must not interfere with the type of non-invasive scan technology that will be employed to capture a scan/digital image of the dental impression.

According to additional and related aspects of the invention, a shipping container is provided that is configured to store, protect, and transport a set of dental impressions (e.g., a maxillary impression and mandibular impression). In such embodiments, the shipping container includes an exterior surface that houses a first compartment that is configured to store a first dental impression and a second compartment that is configured to store a second dental impression. Similar to the first embodiment described above, the shipping container includes a support located in each of the first compartment and second compartment, with each support being configured to receive an impression tray that includes a patient's dental impression. In addition, each support will include a means attached to or integrally formed with the support that is configured to hold the impression tray in place on the support and to position the impression tray in a standardized orientation.

According to yet further related aspects of the invention, methods for capturing a digital image of a dental impression are provided (and, as an extension of such methods, for producing a digital model of a patient's dentition based on the digital image). The methods generally include the step of placing a dental impression that is located within an impression tray within a shipping container described herein (which has the benefit of securing and holding the impression in a standardized orientation, within a container that has an exterior surface and internal supports that will not interfere with a selected non-invasive imaging scan). Next, a non-invasive imaging scan of the shipping container and the dental impression contained therein may be captured, e.g., a radiographic imaging scan, magnetic resonance imaging scan, or an ultrasonic imaging scan. Importantly, the invention provides that the non-invasive imaging scan of the shipping container and the dental impression is obtained without the need to open the shipping container (or directly handle the dental impression(s) contained therein). In certain embodiments, the methods of the present invention may further include providing the non-invasive imaging scan to a computer program that is configured to produce a digital model of a patient's dentition, based on the non-invasive imaging scan.

The above-mentioned and additional features of the present invention are further illustrated in the Detailed Description contained herein.

DETAILED DESCRIPTION OF THE INVENTION

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used, and made without departing from the scope and spirit of the invention.

Figure 1:
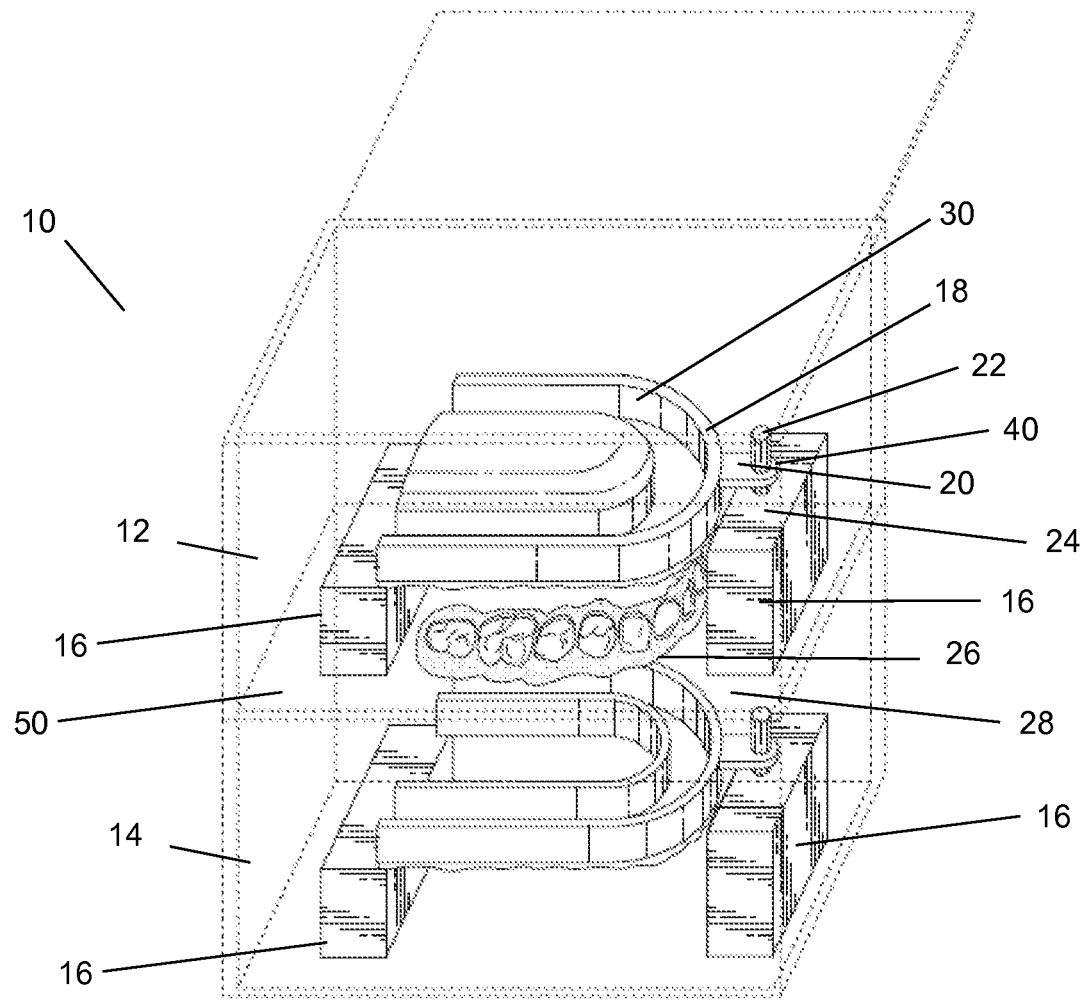
FIG. 1 is an illustration of the shipping container described herein, which includes a first tray that holds a first (e.g., maxillary) impression and a second tray that holds a second (e.g., mandibular) impression, with a corresponding bite registration located between the two impressions.
Figure 2:
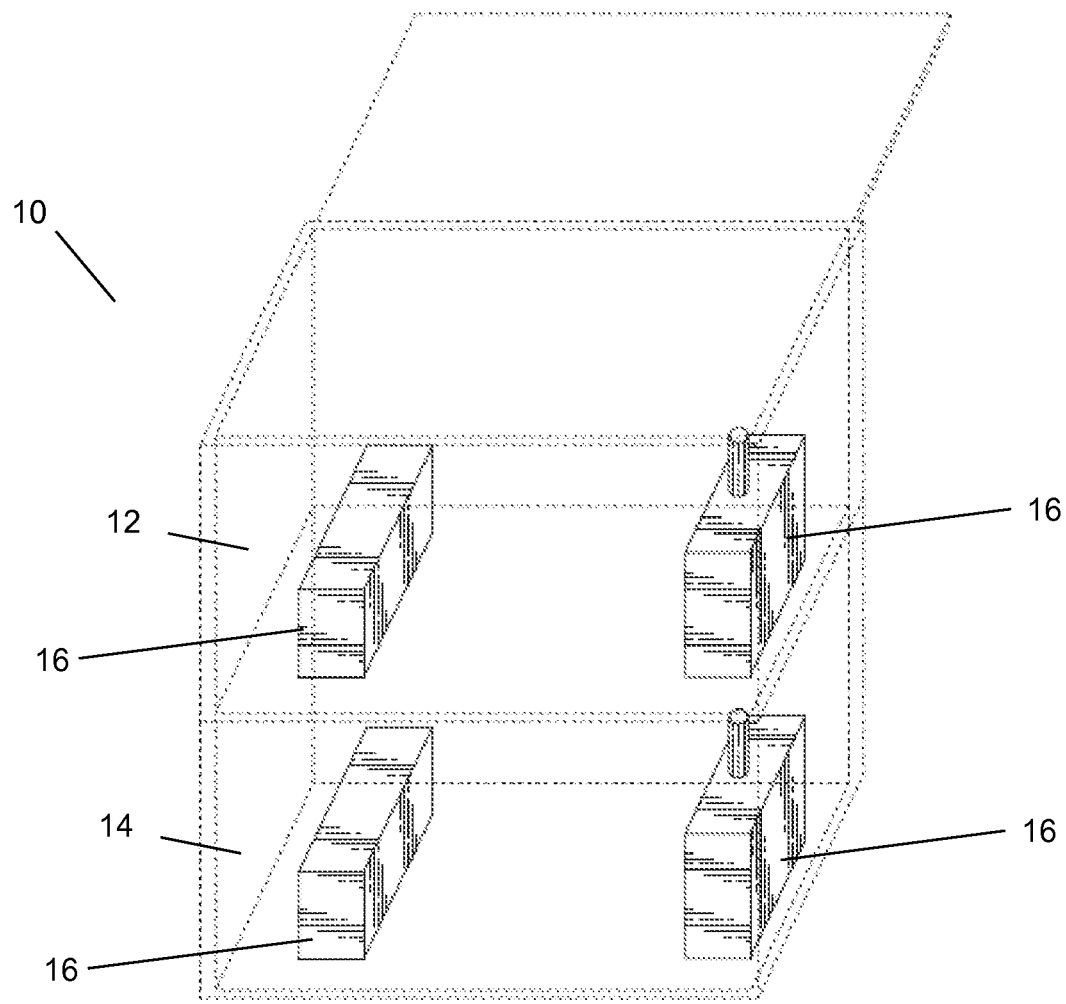
FIG. 2 is an illustration of a non-limiting example of the shipping container described herein and illustrated in FIG. 1.
Figure 3:
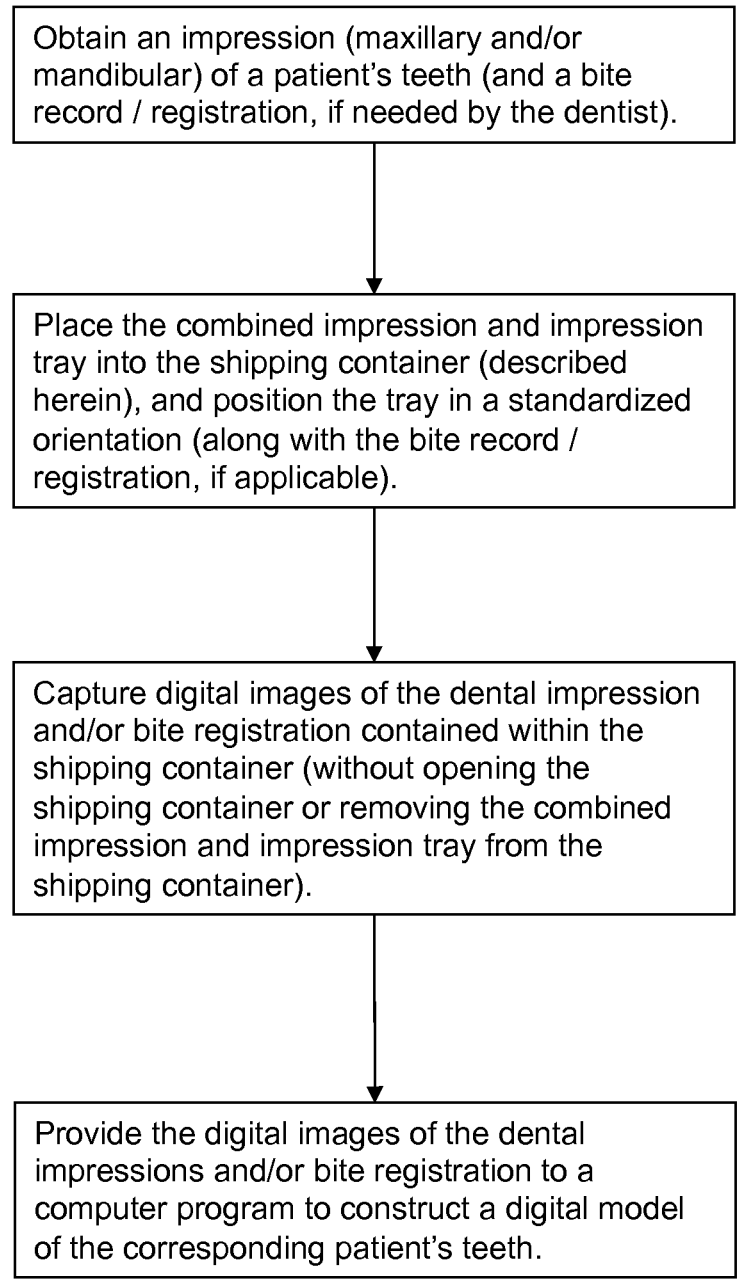
FIG. 3 is a flow diagram that summarizes the methods described herein that can be used to ship and analyze dental impressions.

Referring now to FIGS. 1-3, according to certain preferred embodiments of the present invention, a lightweight dental impression shipping container 10 is provided. The invention provides that the shipping container 10 may contain a single compartment 12, which is configured to hold a patient's maxillary impression or mandibular impression. Alternatively, the shipping container 10 may contain a first compartment 12 and second compartment 14 (with a dividing floor 50 separating the compartments), with each such compartment being configured to hold a separate impression. In such embodiment, the shipping container 10 is configured to hold and transport both a maxillary impression and mandibular impression of a single patient, along with (optionally) the patient's bite registration as described below.

According to certain embodiments, the invention provides that the shipping container 10 may be comprised of various materials, which are suitable for the type of impression imaging procedure that will be utilized by the laboratory. In certain embodiments, for example, the shipping container 10 may be comprised of a lightweight cardboard or foam board material. In certain preferred embodiments, the shipping container 10 will preferably include one or more support blocks 16, which are configured to receive the impression tray(s) 18 that are positioned inside the shipping container 10. The support blocks 16 are preferably configured to provide both anterior and posterior support for the impression tray(s) 18 (and the dental impressions contained therein, which may be disposed within a defined space 30 of the impression tray(s) 18), and orient the impressions in a consistent and suitable way for subsequent imaging (as described below). The support blocks 16 are preferably comprised of the same (or similar) material used to construct the outer shell (exterior) of the shipping container 10, such as a lightweight cardboard or foam board material.

In this embodiment, a support block 16 will preferably include a means for engaging, securing, and properly orienting a handle 20 of an impression tray 18. For example, as illustrated in FIGS. 1 and 2, a support block 16 may comprise a rod 22 affixed to (or integrally formed with) a support block 16, which is configured to be disposed through an aperture 40 in the handle 20 of an impression tray 18. In such embodiments, the rod 22 may be oriented to be perpendicular to a top surface 24 of the support block 16. In other embodiments, instead of the perpendicular rod 22 illustrated herein, other means for engaging, securing, and properly orienting a handle 20 of an impression tray 18 in the container 10 may be employed, such as corresponding magnets located on the handle 20 of an impression tray 18 and the support block 16, corresponding loop-and-hook attachment materials, a slot or indentation may be formed in the top surface 24 of the support block 16 that is configured to receive the tray 18 handle 20, mechanical mating elements other than a cylindrically-shaped rod 22 (e.g., a rectangular protrusion and a corresponding square aperture in the handle 20 of the impression tray 18), or other mechanical attachment means may be employed.

In the non-limiting embodiments shown in FIGS. 1 and 2, the rod 22 of the support block 16, and the aperture 40 in the impression tray 18 handle 20, allow the impression tray 18 to be easily and quickly placed into the shipping container 10. Such components further enable the impression tray 18 to be oriented in the shipping container 10 in a standardized manner. The invention provides that consistent orientation of the impression tray 18 among a plurality of shipping containers 10 allows for impression processing procedures (at the dental laboratory) to be standardized. Such standardization also renders the impressions amenable to imaging techniques and subsequent digital modeling (e.g., employing computer programs and algorithms to fit and interdigitate the maxillary and mandibular teeth impressions).

According to further embodiments of the present invention, the shipping containers 10 may be configured to receive, store, and transport a patient's bite registration 26 (a mold or other tangible replica of a patient's dental bite registration). In such embodiments, the shipping containers 10 may be configured to receive, store, and transport the bite registration 26 on a surface 28 of the container 10 located between, for example, the maxillary and mandibular impressions. In such embodiments, the bite registration 26 is preferably secured and protected by the anterior and posterior support blocks 16 shown in FIGS. 1 and 2.

The invention provides that the shipping containers 10 described herein, along with the dental (maxillary and/or mandibular) impressions (located in space 30 of the impression tray 18) and bite registration 26 contained therein, may be imaged using non-invasive imaging technologies. The invention provides that the material used to construct the shipping containers 10 and its internal components will be determined by the type of non-invasive imaging technology employed. For example, in certain preferred embodiments, radiographic imaging systems (such as cone-beam computed tomography or spiral computed tomography) may be used to image the dental impressions held within a shipping container 10. In such embodiments, the invention provides that the shipping container 10 and impression tray 18 are preferably comprised of acrylic or plastic materials, which will not interfere with radiographic (x-ray) imaging (and the subsequent creation of a digital model of the impressions). Other suitable materials include paper, cardboard, plastics, foam, Styrofoam, and low density woods (such as balsa wood).

When the shipping containers 10, along with the dental (maxillary and/or mandibular) impressions and bite registration 26 contained therein, are imaged using magnetic resonance imaging (MRI), materials that do not significantly interfere with a magnetic signal should be used to construct the shipping container 10 and impression tray 18. More particularly, in such embodiments, low-water content materials should be employed, such as paper, cardboard, plastics and foam. By way of further example, when ultrasonic imaging is used, the shipping container 10 and impression tray 18 should consist of materials that do not significantly interfere with sound waves, such as foam and thin paper materials. In addition, in certain embodiments, the invention provides that the shipping container 10 and impression tray 18 may be comprised of custom or composite materials, which are designed for the specific type of non-invasive imaging techniques employed. In still further embodiments, the materials may be designed to be bio-degradable and/or recyclable.

According to yet further embodiments, the invention provides that the shipping container 10 may further include one or more materials that are configured to combat elevated temperatures and humidity levels. Extremely high temperatures and/or humidity levels may compromise the integrity of a dental impression. The invention provides that by fabricating the shipping container 10 with layers of cardboard (including corrugated cardboard), foam board, plastic wraps, and similar materials, the internal area of the shipping container 10 may be more insulated from extreme temperatures. Similarly, the shipping container 10—including its internal area—may be provided with supplementary amounts of water absorbent materials (fillers), such as foams, sponge materials, cotton, etc., which will serve to mitigate the effects of excessive humidity (along with a tight seal, e.g., plastic sealant, around the perimeter of the shipping container 10).

The shipping containers 10 of the present invention are configured to store, secure, and protect dental impressions in transit from a dental office to a processing laboratory—and, furthermore, to render the dental impressions suitable for high-throughput non-invasive imaging (and subsequent digital modeling). Referring to FIG. 3, the invention further encompasses methods of capturing digital images/scans of dental impressions using the shipping containers 10 described herein, such that the images may be used to construct digital models of the corresponding patient's teeth. The digital models may then be used by the laboratory to design and produce certain restorations (e.g., crowns and bridges), guides for surgery, splints, dentures, bleaching trays, orthodontic appliances and other products for the corresponding patients (which are provided back to the dentist who obtained the initial impression).

The invention provides that such methods generally entail obtaining an impression (maxillary and/or mandibular) of a patient's teeth; placing the combined impression and impression tray 18 into the shipping container 10 in a secure and standardized orientation (as described above); and capturing digital images of dental impressions and/or bite registration 26 contained within the shipping container 10 (without opening the shipping container 10 or removing the combined impression and impression tray 18 from the shipping container 10). The invention provides that the digital images of the dental impressions and/or bite registration 26 may then be used by known and currently-available computer programs to construct a digital model of the corresponding patient's teeth. Following the imaging analysis, the invention provides that the shipping container 10 (and its contents) may be discarded, destroyed, or returned to the dentist.

In certain embodiments, the exterior of the shipping container 10 will contain encrypted information, writings, serial numbers, or other indicia (e.g., bar codes) that may be reviewed and/or scanned, which help the receiving laboratory correlate each shipping container 10 with the images, digital model, and dental products that the laboratory will create using the methods outlined above. In order to maintain compliance with HIPAA and other privacy laws, the invention provides that such information, writings, serial numbers, or other indicia will preferably be encrypted, since the information, writings, serial numbers, or other indicia may reside on the exterior of the shipping container 10 and, therefore, be viewable to others (such as the carriers who transport the shipping container 10 from the dentist to the laboratory). The invention provides that the dentist and/or laboratory will maintain a database and key to decrypt the information, writings, serial numbers, or other indicia, such that each shipping container 10 and dental impression (along with the image data, digital model, and dental products derived therefrom) may be matched with the applicable patient There are many significant advantages provided by the present invention. For example, the shipping container 10 described herein is configured to not only provide a suitable means for storing, transporting, and protecting a dental impression in transit from a dentist to a laboratory, the shipping container 10 is also configured to enable the impression to be imaged using non-invasive means without opening the shipping container 10 or directly handling the impression contained therein. Accordingly, the laboratory avoids the need to open the shipping container 10 and to disinfect the impression (and handle the toxic chemicals associated with such procedures). This saves the laboratory time, human resources, and money—and it alleviates the administrative burdens and expense associated with handling toxic chemicals. Still further, in view of the standardized manner by which the impression is held within the shipping container 10, the invention provides that the imaging process and subsequent digital model building steps described herein may be automated by the laboratory (with little-to-no human intervention).

The many aspects and benefits of the invention are apparent from the detailed description, and thus, it is intended for the following claims to cover all such aspects and benefits of the invention which fall within the scope and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed is:

1. A shipping container with an enclosed dental impression, wherein the shipping container is configured to store, protect, and transport the dental impression, wherein the shipping container comprises:
   (a) an exterior surface that encloses an interior area;
   (b) an impression tray, located within the interior area, which holds the dental impression;
   (c) a support located within the interior area that is configured to receive the impression tray, wherein the support consists of a first support block that receives an anterior side of the impression tray and a second support block that receives a posterior side of the impression tray; and
   (d) a means attached to or integrally formed with the first support block, wherein said means is configured to hold the impression tray in place on the support and to position the impression tray in a standardized orientation that is suitable for capturing a digital image of the dental impression, wherein the exterior surface and support are comprised of a material that will not interfere with a selected non-invasive imaging scan used to capture the digital image.

2. The shipping container and dental impression of claim 1, wherein the means attached to or integrally formed with the support is a rod that extends perpendicular from a top surface of the support.

3. The shipping container and dental impression of claim 2, wherein the impression tray includes a handle and an aperture located in the handle, wherein the rod is configured to be disposed through the aperture, such that the impression tray is held in place on the support and is positioned in the standardized orientation.

4. The shipping container and dental impression of claim 3, wherein the exterior surface and support are comprised of a material selected from the group consisting of acrylic materials, plastic materials, paper, cardboard, foam, and wood materials, when the non-invasive imaging scan is a radiographic imaging scan.

5. The shipping container and dental impression of claim 4, which further comprises an area that is configured to receive and hold a patient's bite registration.

6. A shipping container and a set of enclosed dental impressions, wherein the shipping container is configured to store, protect, transport, and maintain suitable environmental conditions for the set of dental impressions, wherein the shipping container comprises:
   (a) an exterior surface that houses a first compartment that is configured to store a first dental impression and a second compartment that is configured to store a second dental impression;
   (b) a first impression tray, located in the first compartment, which holds the first dental impression; and a second impression tray, located in the second compartment, which holds the second dental impression;
   (c) a first support located in the first compartment that is configured to receive the first impression tray and a second support located in the second compartment that is configured to receive the second impression tray, wherein the first support consists of a first support block that receives an anterior side of the first impression tray and a second support block that receives a posterior side of the first impression tray, and the second support consists of a third support block that receives an anterior side of the second impression tray and a fourth support block that receives a posterior side of the second impression tray; and
   (d) a means attached to or integrally formed with each of the first support block and second support block that is configured to hold each impression tray in place on the support and to position each impression tray in a standardized orientation that is suitable for capturing a digital image of the dental impression, wherein the exterior surface and supports are comprised of a material that will not interfere with a selected non-invasive imaging scan used to capture the digital image.

7. The shipping container and the set of dental impressions of claim 6, wherein the means attached to or integrally formed with each support is a rod that extends perpendicular from a top surface of each support.

8. The shipping container and the set of dental impressions of claim 7, wherein each impression tray includes a handle and an aperture located in the handle, wherein the rod is configured to be disposed through the aperture, such that the impression tray is held in place on the support and is positioned in the standardized orientation.

9. The shipping container and the set of dental impressions of claim 8, wherein the exterior surface and supports are comprised of a material selected from the group consisting of acrylic materials, plastic materials, paper, cardboard, foam, and wood materials, when the non-invasive imaging scan is a radiographic imaging scan.

10. The shipping container and the set of dental impressions of claim 9, which further comprises an area that is configured to receive and hold a patient's bite registration.

11. The shipping container and the set of dental impressions of claim 10, which further comprises one or more materials that are configured to combat elevated temperatures and humidity levels.

12. A method for capturing a digital image of the dental impression of claim 1, which comprises the steps of:
   (a) placing the dental impression that is located within the impression tray within the shipping container of claim 1; and
   (b) obtaining a non-invasive imaging scan of the shipping container and the dental impression contained therein.

13. The method of claim 12, wherein the non-invasive imaging scan of the shipping container and the dental impression is obtained without opening the shipping container.

14. The method of claim 13, which further comprises providing the non-invasive imaging scan to a computer program that is configured to produce a digital model of a patient's dentition, based on the non-invasive imaging scan.

15. The method of claim 12, which further comprises obtaining a non-invasive imaging scan of the shipping container and a patient's bite registration contained therein.

16. The method of claim 15, wherein the non-invasive imaging scan is a radiographic imaging scan, magnetic resonance imaging scan, or an ultrasonic imaging scan.

17. The method of claim 16, wherein the means attached to or integrally formed with the support is a rod that extends perpendicular from a top surface of the support.

18. The method of claim 17, wherein the impression tray includes a handle and an aperture located in the handle, wherein the rod is configured to be disposed through the aperture, such that the impression tray is held in place on the support and is positioned in the standardized orientation.

* * * * *